US00PP22340P2

(12) United States Plant Patent
Hoefnagels

(10) Patent No.: US PP22,340 P2
(45) Date of Patent: Dec. 13, 2011

(54) ***BEGONIA* PLANT NAMED 'FEDOR'**

(50) Latin Name: *Begonia rex*
Varietal Denomination: Fedor

(75) Inventor: Antoon Hoefnagels, Lent (NL)

(73) Assignee: Douglas Cole

( * ) Notice: Subject to any disclaimer, the term of this patent is extended or adjusted under 35 U.S.C. 154(b) by 0 days.

(21) Appl. No.: 12/799,990

(22) Filed: May 5, 2010

(51) Int. Cl.
*A01H 5/00* (2006.01)
(52) U.S. Cl. ..... Plt./343
(58) Field of Classification Search ..... Plt./343
See application file for complete search history.

*Primary Examiner* — June Hwu
(74) *Attorney, Agent, or Firm* — Cassandra Bright

(57) ABSTRACT

A new and distinct *Begonia rex* named 'Fedor' is disclosed, characterized by its unique silver foliage with dark veins, medium sized leaves and ease of propagation. The new cultivar is a *Begonia rex*, typically suited for ornamental container use.

1 Drawing Sheet

Figure 1:
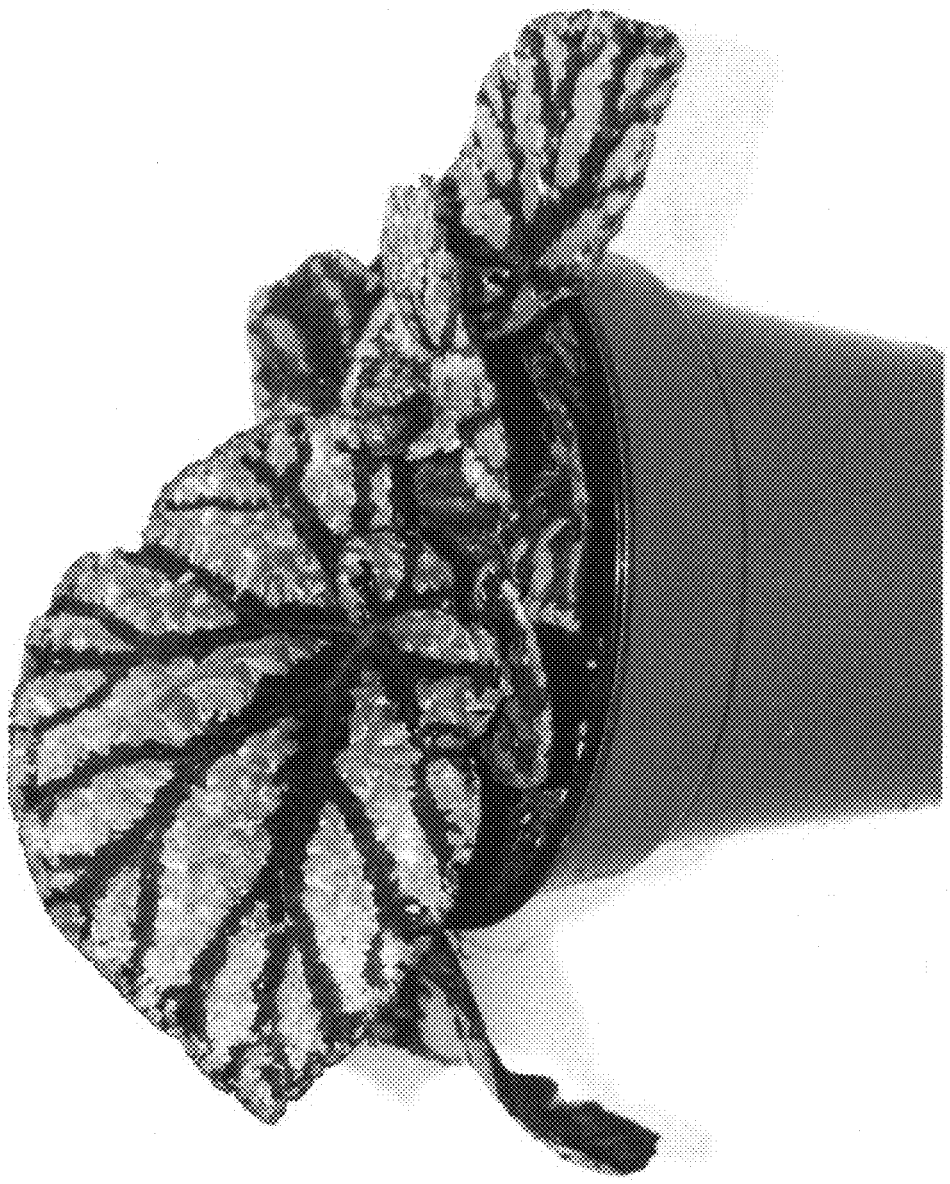

Latin name of the genus and species: *Begonia rex*.
Variety denomination: 'Fedor'.

BACKGROUND OF THE INVENTION

The new cultivar is the result of a planned breeding program of *Begonia rex*. The new variety originated from the crossing of the female parent, the unpatented variety of *Begonia rex* 'Volcano' with the pollen parent, the unpatented proprietary seedling referred to as 'U288.' The new variety was discovered by the inventor in the summer of 2005 at a commercial greenhouse in Lent, the Netherlands.

After selecting and isolating the new cultivar, asexual reproduction of the new cultivar 'Fedor' was first performed in the same commercial greenhouse by vegetative cuttings in the winter of 2005. 'Fedor' has since produced several generations and has shown that the unique features of this cultivar are stable and reproduced true to type.

SUMMARY OF THE INVENTION

The cultivar 'Fedor' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Fedor.' These characteristics in combination distinguish 'Fedor' as a new and distinct *Begonia* cultivar:

1. Consistent silver foliage color, with dark, contrasting mid vein coloration.
2. Medium sized leaves, appropriate for commercial containers.
3. Easy branching, and rooting, resulting in easier commercial propagation.

PARENTAL COMPARISON

Plants of the new cultivar 'Fedor' are similar to the seed parent 'Volcano' in most horticultural characteristics. However, 'Fedor' differs in producing silver foliage with dark veins, where as 'Volcano' has red foliage. Plants of 'Fedor' differ from the pollen parent in that the pollen parent has green foliage, and is much more pubescent.

COMMERCIAL COMPARISON

Plants of the new cultivar 'Fedor' are best compared to the parent variety 'Volcano'.

BRIEF DESCRIPTION OF THE PHOTOGRAPH

The accompanying photograph in FIG. 1 illustrates in full color a typical plant of 'Fedor' grown indoors in Camarillo, Calif. This plant is approximately 12 weeks old, shown in a 4 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'Fedor' plants grown indoors in Camarillo, Calif. during the Winter and Spring months. Temperatures ranged from Approximately 15° C. to 20° C. at night to 15° C. to 25° C. during the day. No artificial light, photoperiodic treatments or chemical treatments were given to the plants. Measurements and numerical values represent averages of typical plant types.

Botanical classification: *Begonia rex* 'Fedor'
Age of the plant described: Approximately 12 weeks.
Container size of the plant described: 4 inch commercial container.

PROPAGATION

Time to initiate roots: Summer: 20 to 25 days at approximately 20° C.

Root description: fine, densely branched, non-fibrous, non-fleshy, colored near Grey-Brown N199A.

PLANT

Growth habit: Outwardingly growing, slightly mounding.
Pot size of plant described: 4 inch.
Height: Approximately 10 cm from soil line to top leaf
Plant spread: Approximately 20 cm.
Growth rate: Moderate.
Branching characteristics: Leaves emerge from 1 large basal clump.
Length of primary lateral branches: No actual branches, individual leaves arise from base. Please see petiole description.

FOLIAGE

Leaf:

*Arrangement.*—Emerging irregularly basally.
*Average length.*—10.5 cm.
*Average width.*—7.5 cm.
*Shape of blade.*—Asymmetrical deltoid.
*Apex.*—Acute.
*Base.*—Cordate.
*Margin.*—Crenulate, very slightly crisped and ciliate.
*Texture of top surface.*—Shiny, rugulose.
*Pubescence.*—Upper Surface: Sparsely hispid, hairs occurring approximately 1 cm apart. Approximately 0.1 cm in length colored near Orange-White 159B, turning Greyed-Red 180D near tip. Lower Surface: Hirsute hairs on veins only. Approximately 0.1 cm long, colored near RHS Greyed-Purple 185B.
*Aspect.*—Slightly concave from mid-vein. Slightly undulating as leaf ages.
*Color.*—Young foliage upper side: Background color, near -Green 138D, blotches along veins near petiole attachment Greyed-Green N189A, blotches near veins closer to margins near Green 137A. Margin near Greyed-Purple 187A. Young foliage under side: Background color, near RHS Green 138B. Veins and thin blotches near veins near Red-Purple 59A. Margin, near Greyed-Purple 187A. Mature foliage upper side: Background color, near Greyed-Green 191C. blotches along veins near petiole attachment Greyed-Purple N186B, blotches near veins closer to margins near Green 137A. Margin background colored near Greyed-Green 189C with very edge of margin Greyed-Purple N186C. Small blotches on margin near Greyed-Purple N186A. Mature foliage under side: Background color, near RHS Green 138B. Veins and thin blotches near veins near Red-Purple 59A. Overlying blush throughout underside of leaf near Red-Purple 59A. Margin, near Greyed-Purple 187A.
*Venation.*—Type: Pinnate. Venation color upper side: Near RHS Green 138B, changing to the color of the leaf blade near margin. Venation color under side: Near RHS Red-Purple 59A.
*Petiole.*—Length: Approximately 2.8 cm. Diameter: Approximately 0.5 cm. Color: Near RHS Greyed-Purple 187A. Surface: Vilous. Hairs colored near RHS Greyed-Purple 184B, approximately 0.15 cm long, fine and undulating.
*Stipule description: Shape: Deltoid. Length: Approximately* 1.2 cm. Diameter: Approximately 1.1 cm at widest point. Color: Near RHS Greyed-Red 180A. Texture: Villous.

FLOWER

Flowering not observed to date in this variety.

OTHER CHARACTERISTICS

Seeds and fruits: Not observed to date.
Disease/pest resistance: Neither resistance nor susceptibility to normal diseases and pests of *Begonia.*
Temperature tolerance: The new variety tolerates temperatures from approximately −2° C. to 35° C.

What is claimed is:

1. A new and distinct cultivar of *Begonia rex* plant named 'Fedor' as herein illustrated and described.

* * * * *